United States Patent [19]
Asakura et al.

[11] Patent Number: 5,752,425
[45] Date of Patent: May 19, 1998

[54] MICROTOME

[75] Inventors: Kentaro Asakura; Yasuhisa Hirohata, both of Tokyo; Nobuyoshi Kataoka, Sakado, all of Japan

[73] Assignee: Chuo Precision Industrial Co., Ltd., Tokyo, Japan

[21] Appl. No.: 756,905

[22] Filed: Dec. 2, 1996

[30] Foreign Application Priority Data

Dec. 25, 1995 [JP] Japan .................. 7-350943

[51] Int. Cl.$^6$ ........................................ G01N 1/06
[52] U.S. Cl. .................. 83/713; 83/76.9; 83/412; 83/915.5
[58] Field of Search ............... 83/703, 707, 713, 83/714, 717, 718, 76.6, 76.9, 915.5, 412, 414

[56] References Cited

U.S. PATENT DOCUMENTS

| | | | |
|---|---|---|---|
| 3,138,749 | 6/1964 | Stibitz | 83/915.5 X |
| 3,293,972 | 12/1966 | Burkhardt et al. | 83/915.5 X |
| 3,702,604 | 11/1972 | Jones | 83/915.5 X |
| 3,828,641 | 8/1974 | Sitte | 83/915.5 X |
| 3,975,977 | 8/1976 | Momberg | 83/915.5 X |
| 4,126,069 | 11/1978 | Shimonaka | 83/703 |
| 5,461,953 | 10/1995 | McCormick | 83/915.5 X |

*Primary Examiner*—Eugenia Jones
*Attorney, Agent, or Firm*—Oblon, Spivak, McClelland, Maier & Neustadt, P.C.

[57] ABSTRACT

A microtome particularly suitable for sectioning specimen to be observed on a transmission type electron microscope. Mounted on top of and located to one side of a machine base (2) are an X-Y axis stage and a tilting stage (4) which in turn supports thereon a cutter holder block (5) with a cutting knife (6). Located to the other side of the machine base (2) is a micro-feed mechanism (7) which supports thereon a specimen holder support arm (12) with specimen (14) and a Z-axis stage (11). The micro-feed mechanism (7) has first and second linear motor stages (8) and (9) to be displaced inversely in intersecting directions crossed each other with a predetermined intersection angle (28) across Y-axis. As the first and second linear motor stages (8) and (9) are displaced at the intersection angle (20) with each other, the specimen (14) is displaced over a small distance of nanometrically fine level in the direction of X-axis, thereby permitting to produce an ultra-thin specimen piece.

7 Claims, 8 Drawing Sheets

MICROTOME

BACKGROUND OF THE INVENTION

1. Field of the Art

The present invention relates to a microtome for preparing ultra-thin specimen pieces to be examined, for example, on an electron microscope or the like.

2. Prior Art

In microscopic observation of minute micro-level structures of a specimen by the use of a transmission electron microscope (hereinafter referred abbreviated as "TEM" for brevity), specimen pieces are usually prepared by either microtomical sectioning method, replica method, negative dying method, shadowing method and so forth. Of these method, the microtomical ultra-sectioning method is generally used as standard technology in preparing specimens for TEM observations.

In order to observe a transmission image of micro-level structures in a specimen on a TEM, it is imperative requisite for the specimen to be thin enough to ensure transmission of electron rays therethrough. More specifically, specimen materials have to be cut into ultra-thin pieces of 50 nm to 70 nm in thickness. For this reason, microtomes are essential to research involving TEM observations.

Conventional microtomes are generally constituted by a machine base, a cutter holder block fixedly mounted in one side portion on the machine base and holding a cutting knife of glass or diamond, a specimen holder block fixedly mounted in the other side portion on the machine base, a cutting mechanism positioned on the side of the specimen holder block for slicing off a thin section of a specimen material by moving same relative to the cutting knife, and a micro-feed mechanism capable of feeding the specimen holder block or the cutter holder block over an infinitesimally small distance toward the other.

The micro-feed mechanism can be a mechanical feed type using feed screws in combination with leverage, or a thermal expansion feed type using thermal expansion of electric bulbs or the like.

No matter whether mechanical feed type or thermal expansion type, micro-feed mechanisms on prior art microtomes invariably have limitations in unit feed distance.

In case of a mechanical type micro-feed mechanism using a stepping motor for turning a feed screw, for the purpose of eliminating limitations in unit feed distance, it has been the general practice to resort to a ball screw, thereby translating a rotational movement into a linear movement. Therefore, high precision micro-feed has been difficult in most cases due to loose saccadic movements or backlashes of a ball screw or other mechanical parts, resulting in inferior positioning accuracy.

SUMMARY OF THE INVENTION

In view of the above-mentioned problems of the prior art, it is an object of the present invention to provide a microtome with a micro-feed mechanism which can easily make high precision micro-feeds of nanometrically fine level for cutting off ultra-thin sections of specimen.

In accordance with the present invention, the above-stated objective is achieved by the provision of a microtome which essentially includes: a machine base; a first holder means located on the machine base for holding either one of cutting knife and specimen; a micro-feed mechanism located on the machine base in face to face relation with the first holder means in the direction of X-axis and having first and second feed means to displaced in intersecting directions crossing at a small intersection angle $2\theta$ across Y-axis to make a feed of an extremely fine level in the direction of X-axis; and a second holder means located on the micro-feed mechanism in face to face relation with the first holder means to hold thereon the other one of the cutting knife and specimen.

With the arrangements just described, the first feed means of the micro-feed mechanism is displaced in a direction at an angle of $+\theta$ with Y-axis while the second feed means is displaced in a direction at an angle of $-\theta$ with Y-axis. Therefore, each time the second feed means of the micro-feed mechanism can be fed in an extremely fine level in the direction of X-axis according to the intersection angle $2\theta$ of the directions of movements of the first and second feed means. Consequently, for example, in case the cutting knife and specimen are set on the first and second feed means of the micro-feed mechanism, respectively, an ultra-thin specimen pieces can be produced by cutting off the specimen in a thickness equivalent to the micro-feed distance.

In this instance, the first feed means of the micro-feed mechanism may be constituted by a first fixed member which is securely fixed on the machine base and a first movable member which is movably mounted on top of the first fixed member for movements in a direction at an angle of $+\theta$ with Y-axis, while the second feed means is constituted by a second fixed member which is securely fixed on the first movable member and a second movable member which is movably mounted on top of the second fixed member for movements in a direction at an angle of $-\theta$ with Y-axis.

Further, the first and second feed means of the micro-feed mechanism can be constituted by a linear motor stage including a guide for linearly guiding movement of the movable member relative to the fixed member, magnets fixedly mounted on the part of the fixed member, and coils mounted on the part of the movable member and supplied with current to generate magnetic fields acting against the magnets on the fixed member for displacing the movable member.

In case a linear motor stage is used for the feed means in this manner, it becomes possible to realize high precision positioning and smooth movements of the feed mechanism, free of mechanical saccadic movements or back-lashes as experienced with ball screws which are generally used for translating rotational movements into rectilinear feeding movements.

In one preferred form of the present invention, there is provided a microtome which is constituted by: a machine base; a first linear stage located on the machine base for movements in the directions of X- and Y-axes; a cutter holder provided on the first linear stage and holding a cutting knife thereon; a micro-feed mechanism including first and second linear motor stages provided on the machine base side by side with the first linear stage in the direction of X-axis, the first linear motor stage being movably mounted on the machine base for displacements in a direction at a small angle $+\theta$ with Y-axis, and the second linear motor stage being movably mounted on top of the first linear motor stage for movements in a direction at a small angle $-\theta$ with Y-axis; a second linear stage movably provided on top of the second linear motor stage for displacements in the direction of Z-axis; a specimen holder support arm provided on the second linear stage and supporting a specimen holder at a fore end thereof in confronting relation with the cutting knife; and a linear stage drive means for driving the specimen holder support arm in the direction of Z-axis along with the second linear stage.

In the case of the microtome of the arrangements just described, the first and second linear motor stages are displaced in two intersecting directions crossing at an intersection angle of 2θ, and the specimen holder support arm is located in an upper lifted position in an initial state in the direction of Z-axis. In this instance, when the first and second linear motor stages are driven over a displacement distance "a", the second linear stage and specimen holder support arm on the second linear motor stage are displaced over a distance of 2a×sin θ toward the opposing cutter holder in the direction of X-axis. In this displaced position, the specimen holder support arm is lifted down by the linear stage drive means, lowering a specimen on the specimen holder support arm toward the cutting knife to cut off an ultra-thin specimen piece. After the sectioning operation, each of the linear motor stages is returned to an initial position, and the specimen holder support arm is lifted up in the direction of Z-axis to return to its initial position.

Further, in another preferred form of the present invention, the microtome is constituted by: a machine base; a first linear stage located on the machine base for movements in the directions of X- and Y-axis; a specimen holder provided on the first linear stage; a micro-feed mechanism including first and second linear motor stages provided on the machine base side by side with the first linear stage in the direction of X-axis, the first linear motor stage being movably provided on the machine base for displacements in a direction at a small angle +θ with Y-axis, and the second linear motor stage being movably provided on top of the first linear motor stage for movements in a direction at a small angle −θ with Y-axis; a second linear stage movably mounted on top of the second linear motor stage for displacements in the direction of Z-axis; a cutter holder support arm provided on the second linear stage; a cutter holder supported on a fore end of the cutter holder support arm and holding a cutting knife for cutting a specimen in confronting relation with the specimen holder; and a linear stage drive means for driving the cutter holder support arm and cutter holder in the direction of Z-axis along with the second linear stage.

In the case of the microtome of the arrangements just described, similarly, when the first and second linear motor stages are driven over a displacement distance "a", the second linear stage and cutter holder support arm on the second linear motor stage are displaced over a distance of 2a×sine θ in the direction of X-axis toward the specimen holder. In this displaced position, the cutter holder support arm is lifted up from beneath by the linear stage drive means, raising a cutter knife to cut off a specimen on the specimen holder into an ultra-thin specimen piece.

BRIEF DESCRIPTION OF THE DRAWINGS

The above and other objects, features and advantages of the present invention will become apparent from the following description, taken in conjunction with the accompanying drawings which show by way of example preferred embodiments of the invention and in which.

DESCRIPTION OF PREFERRED EMBODIMENTS

Hereafter, the present invention is described more particularly by way of its preferred embodiments with reference to the accompanying drawings.

Figure 1:
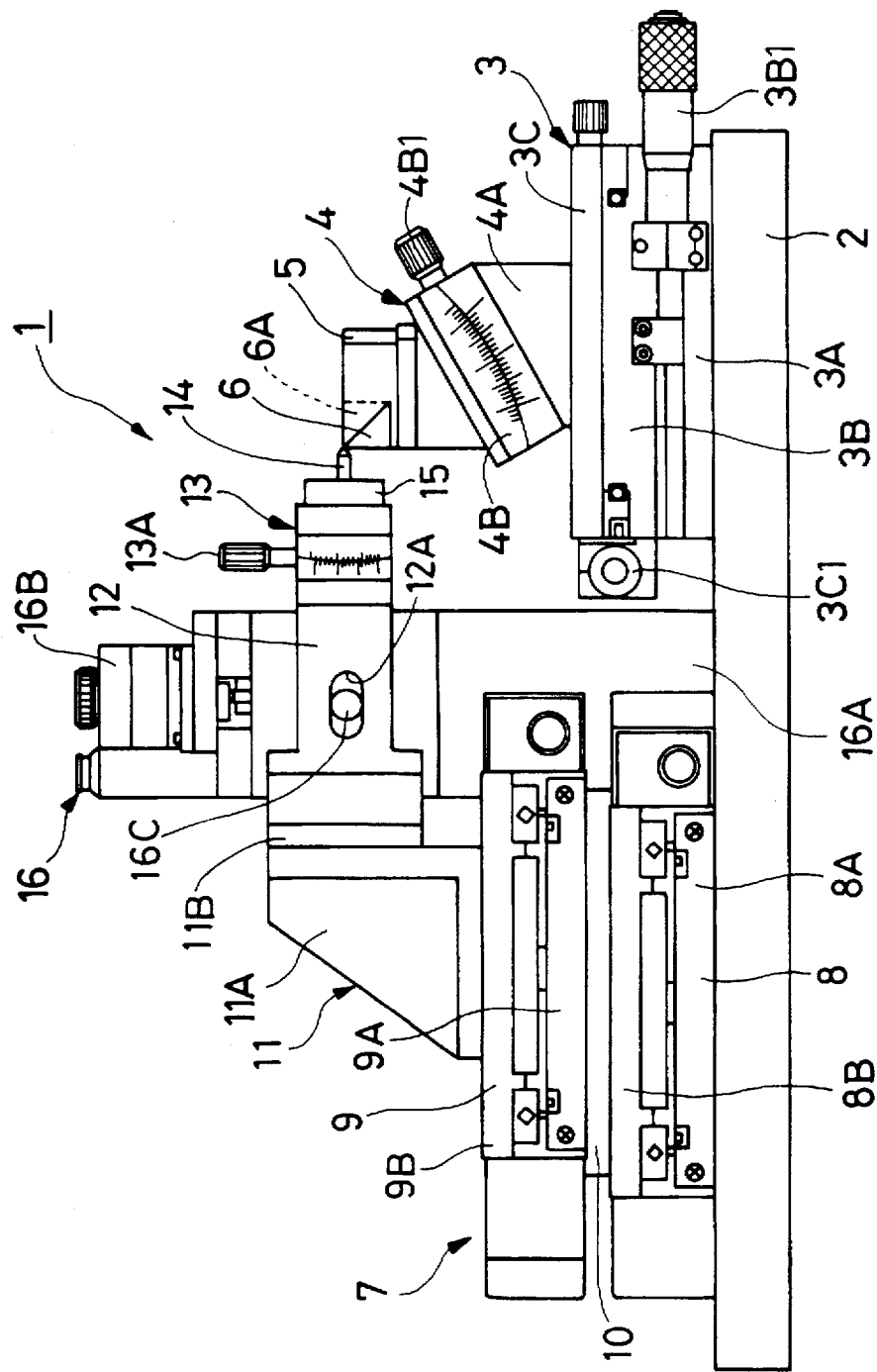
FIG. 1 is a schematic front view of a microtome embodying the present invention.
Figure 2:
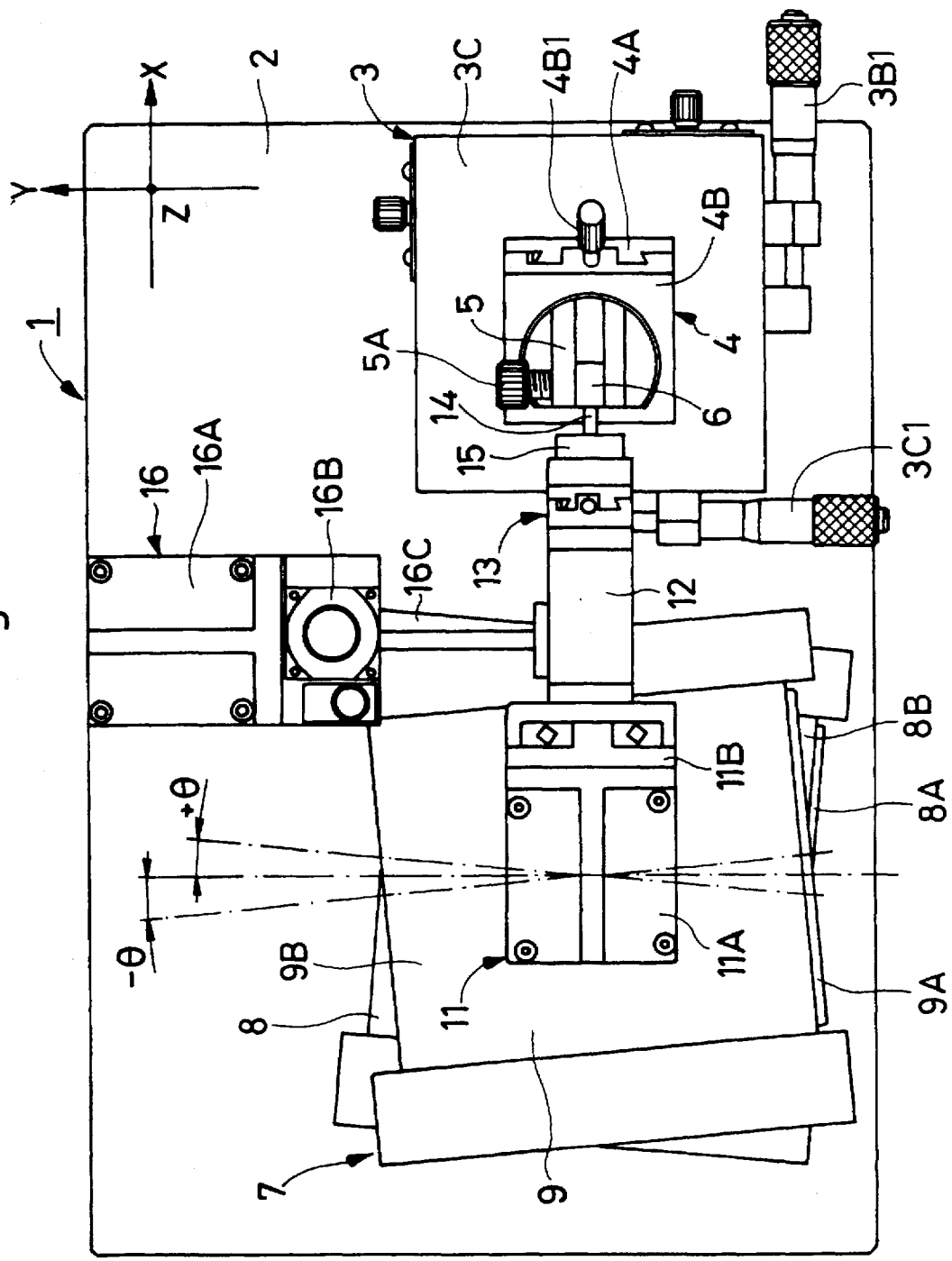
FIG. 2 is a schematic plan view of the microtome of FIG. 1.
Figure 3:
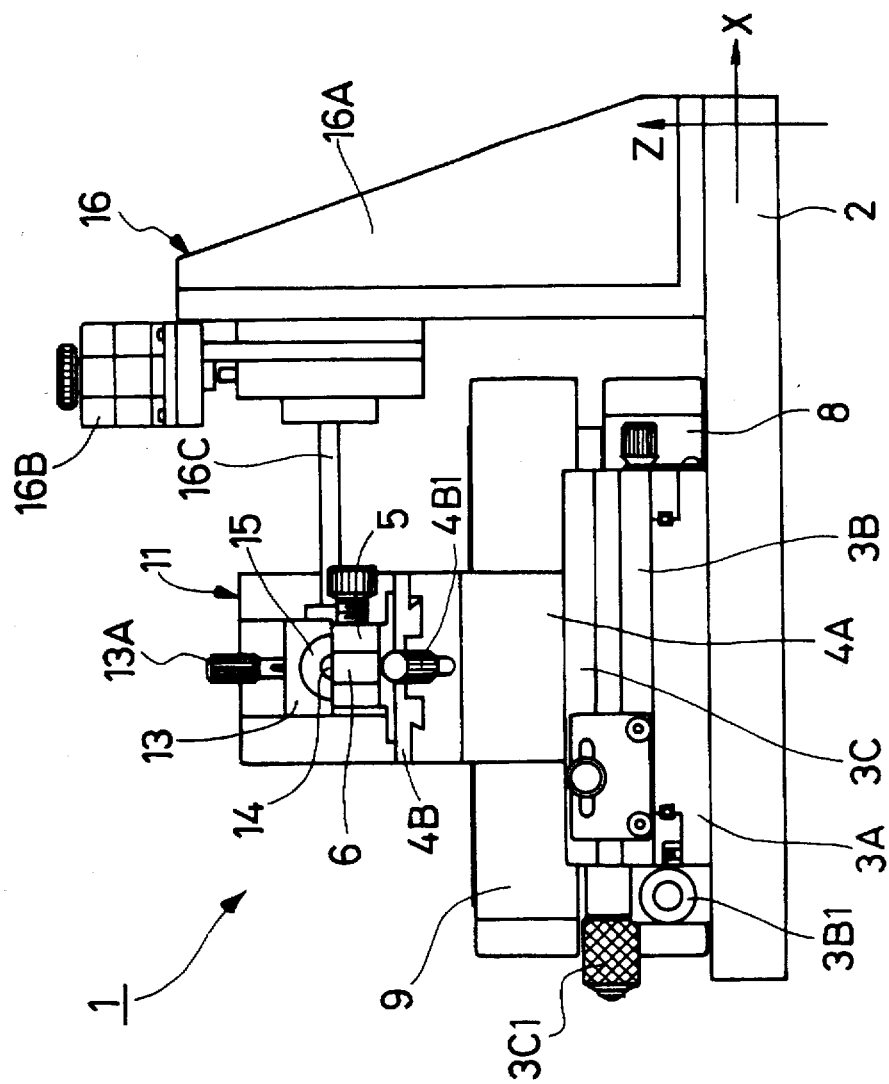
FIG. 3 is a right-hand side view of the microtome of FIG. 1.

Referring to FIGS. 1 through 7, there is shown at 1 a microtome which is adopted as a first embodiment of the present invention. Denoted at 2 is a flat rectangular machine base of cast metallic material. For the convenience of explanation, two directions which are parallel with the face of FIG. 2 are represented by X- and Y-axes, respectively, while a direction perpendicular to the face of the drawing is represented by Z-axis.

Indicated at 3 is an X-Y axis stage which is fixedly mounted in a right portion on the base block 2 as a first linear stage, including a fixed block 3A, a first movable block 3B movably mounted on the fixed block 3A for displacements in the direction of X-axis, and a second movable block 3C movably mounted on the first movable block 3B for displacements in the direction of Y-axis. The position of the first movable block 3B is adjustable in the direction of X-axis by way of an adjusting knob 3B1, while the position of the second movable block 3C is adjustable in the direction of Y-axis by way of an adjusting knob 3C1.

Denoted at 4 is a tilting stage, including a fixed block 4A which is securely mounted on the second movable block 3C of the X-Y axis stage, and a tilting block 4B provided on the fixed block 4A for fine adjustments in the direction of an axis which is inclined relative to X-axis. The angle of inclination of the tilting block 4B is adjustable by way of an adjusting knob 4B1.

Indicated at 5 is a cutter holder block which is fixedly mounted on the tilting block 4B of the tilting stage 4, the cutter holder block 5 having a cutting knife 6 fixed thereon by means of set screws 5A.

The cutting knife 6 is formed of glass, diamond or sapphire in the shape of a prism, and set on the cutter holder block 5 with its cutting edge (of 40° to 60°) on the upper side. Formed behind the cutting knife 6 is a water trough 6A which is filled with distilled water and in which a sectioned specimen piece is collected afloat on distilled water.

The X-Y axis stage 3 plays the role of determining the position of the cutting knife 6 relative to a frozen specimen 14 which will be described hereinlater, while the tilting stage 4 serves to set the angle of the cutting knife 6.

Designated at 7 is a micro-feed mechanism which is provided in a left portion on the base block 2, including a first linear motor stage 8 which is provided on the base block 2 for linear displacements at an angle of +θ with Y-axis, and a second linear motor stage 9 which is provided for linear displacements at an angle of −θ with Y-axis and in an intersecting relation with the first linear motor stage 8. Namely, the first and second linear motor stages 8 and 9 are arranged to be displaced in two intersecting directions at an intersecting angle of 2θ across Y-axis.

Indicated at 10 is a spacer which is interposed between the first and second linear motor stages 8 and 9. The spacer 10 connects a movable block 8B of the first linear motor stage 8 with a fixed block 9A of the second linear motor stage 9 in intersecting relations with each other in terms of directions of linear displacements.

In this instance, the first linear motor stage 8 is arranged as so-called X-axis linear motor stage, and constituted by a fixed block 8A which is fixedly mounted on the machine base 2 side by side with the X-Y axis stage 3 in the direction of X-axis, and a movable block 8B which is movably mounted on top of the fixed block 8A for displacements in a direction at a small angle +θ with Y-axis in the manner as will be described hereinlater. The second linear motor stage 9 is arranged as so-called X-axis linear motor stage and constituted by a fixed block 9A which is fixedly mounted on the above-mentioned movable block 8B, and a movable block 9B which is movably mounted on top of the fixed block 9A for displacements in a direction at a small angle −θ with Y-axis in the manner as will be described hereinlater.

Figure 4:
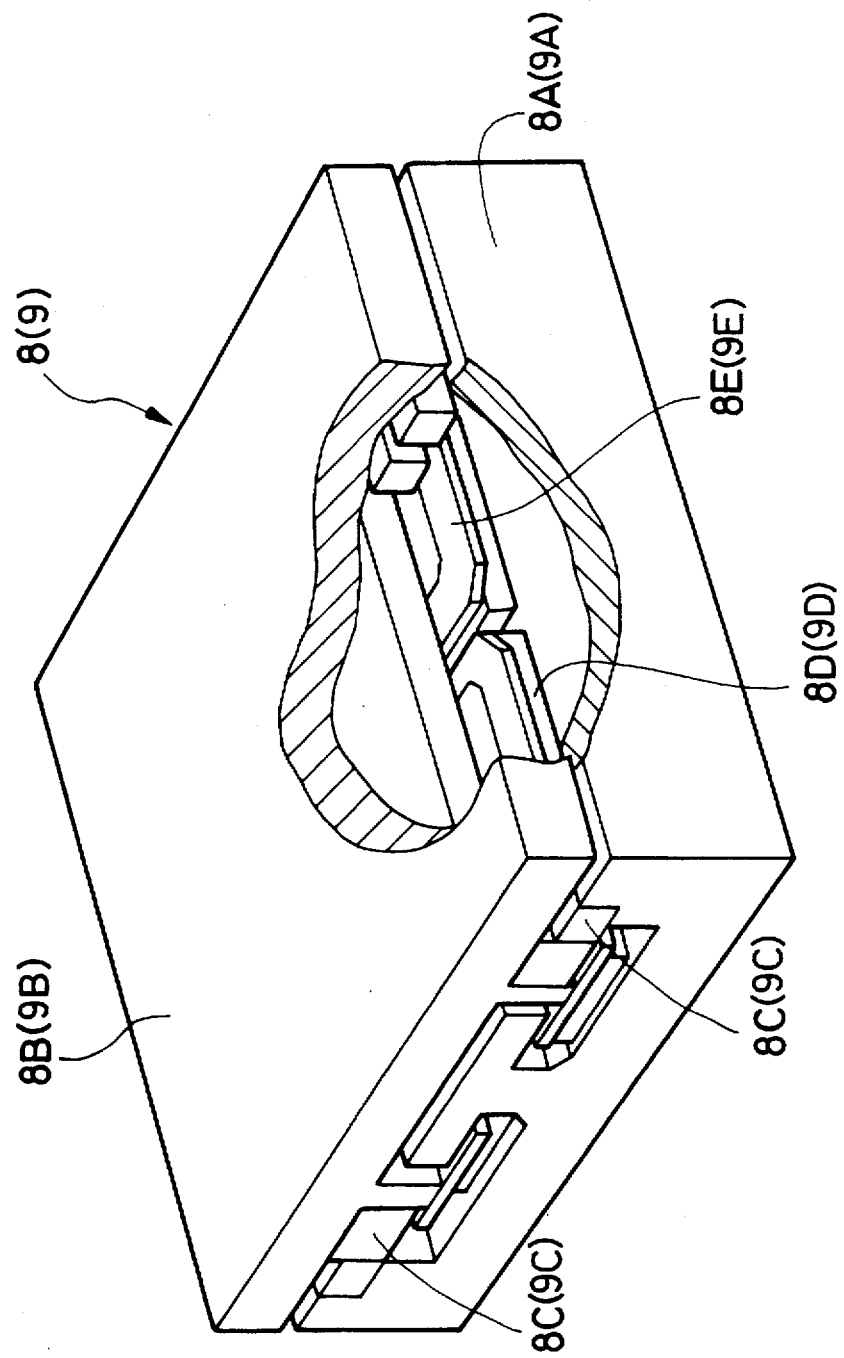
FIG. 4 is a partly cutaway perspective view of a linear motor stage.

As shown in FIG. 4, the first linear motor stage 8 is provided with guide rails 8C for guiding movements of the movable block 8B, magnets 8D provided on the part of the fixed block 8A, and coils 8E provided on the movable block 8B in face to face with the magnets 8D. Upon conducting current through the coils 8E, magnetic fields are generated to displace the movable block 8B relative to the fixed block 8A linearly along the guides 8C through magnetic attracting and repelling actions against magnetic fields of the fixed magnets 8D. The same operating principles apply to the second linear motor stage 9 which is similarly constituted by fixed block 9A, movable block 9B, guide rails 9C, magnets 9D and coils 9E.

Following are some advantages which accrue from the use of the above-described linear motor stages 8, 9 in the micro-feed mechanism 7.

Firstly, since the movable part of each motor is constituted by coils and bobbins and moved rectilinearly, it becomes possible to preclude back-lashes as experienced with ball screws and to reduce the inertial mass. Secondly, as compared with a stepping motor, excellent rectilinearity can be obtained for current and thrust, in addition to a greater instantaneous torque. Thirdly, because of small coil inductance, the linear motor has excellent electrical response characteristics. Fourthly, it is controllable with high precision, free of cogging or other magnetic fluctuations.

In the first linear motor stage 8, the fixed block 8A is securely fixed on the machine base 2 at an angle of +θ with Y-axis, and the movable block 8B on the fixed block 8A is displaceable in one direction which is at an angle of +θ with Y-axis. In the second linear motor stage 9, the fixed block 9A is securely fixed on the movable block 8B at an angle of −θ with Y-axis, and the movable block 9B on the fixed block 9A is displaceable in another direction which is at an angle of −θ with Y-axis. In this instance, the movable blocks 8B and 9B are displaced inversely in the two intersecting directions.

Figure 5:
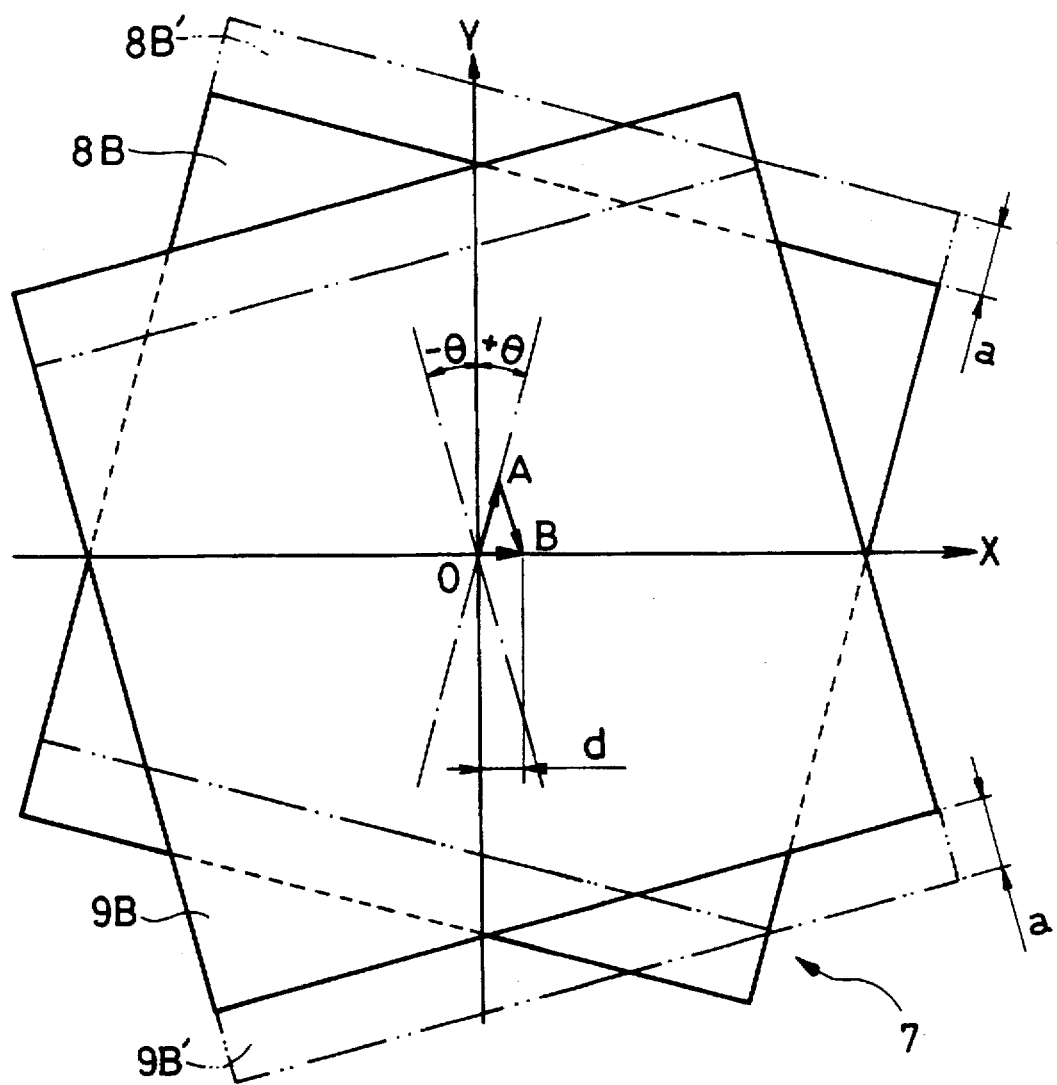
FIG. 5 is a diagrammatic illustration explanatory of movements of a micro-feed mechanism.

In this manner, at the micro-feed mechanism 7, the first and second linear motor stages 8 and 9 are displaced by the same distances "a" as shown in FIG. 5. More specifically, the movable block 8B of the first linear motor stage 8 is displaced by a distance "a" in the direction O-A to advance to the position 8B'. At this time, the distance of displacement of the movable block 8B in the direction of X-axis is "a×sine θ". On the other hand, the movable block 9B of the second linear motor stage 9 is displaced by the same distance "a" in the direction A-B to advance to the position 9B'. At this time, the distance of displacement of the movable block 9B in the direction of X-axis is "a×sine θ". It follows that in overall the movable block 9B of the second linear motor stage 9 is linearly displaced in the direction of X-axis over a distance of "2a×sine θ", which exactly corresponds to a micro-feed distance "d" by the micro-feed mechanism 7 as a whole.

In this regard, for fine feeds of nanometrically fine level, it is preferable to set a small intersecting angle 2θ for the first and second linear motor stages 8 and 9. For example, in case the intersecting angle 2θ is set at 5°, the micro-feed distance "d" becomes as small as d=0.087×a. Namely, the micro-feed distance "d" is smaller than ⅒ of the distance "a" over which each of the first and second linear motor stages 8 and 9 are displaced.

Indicated at 11 is a Z-axis stage or second linear stage, which is constituted by a fixed block 11A and a movable block 11B erected on the movable block 9B of the second linear motor stage 9 of the micro-feed mechanism 7, the movable block 11B being displaceable relative to the fixed block 11A in the direction of Z-axis.

Denoted at 12 is a specimen holder support arm which is extended in the direction of X-axis and which has its base end securely fixed to the movable block 11B of the Z-axis stage 11. A specimen holder 15 which holds a frozen specimen 14 thereon is securely fixed to the fore end of the specimen holder support arm 12 through the tilting stage 13. Formed within the length of the specimen holder support arm 12 is an slot 12A elongated in the direction of X-axis, to receive therein a transmission rod 16C of a Z-axis stage drive which will be described hereinlater. Further, inclination of the above-mentioned specimen 14 is adjustable by way of the adjusting knob 13A of the tilting stage 13. In this instance, a specimen holder block is constituted by the specimen holder support arm 12 and the tilting stage 13.

Designated at 16 is a Z-axis stage drive serving as a linear stage drive means, which is constituted by a standing post 16A erected on the machine base 2, a Z-axis stage drive motor 16B mounted on the upper end of the standing post 16A, and a transmission rod 16C to be moved up and down in the direction of Z-axis by the Z-axis stage drive motor 16B and having its fore end portion received in the aforementioned slot 12A of the specimen holder support arm 12. Upon actuating the Z-axis stage drive motor 16B, the transmission rod 16C is moved in an upward or downward direction to lift up or down the specimen holder support arm 12 along with the movable block 11B of the Z-axis stage 11.

Figure 6:
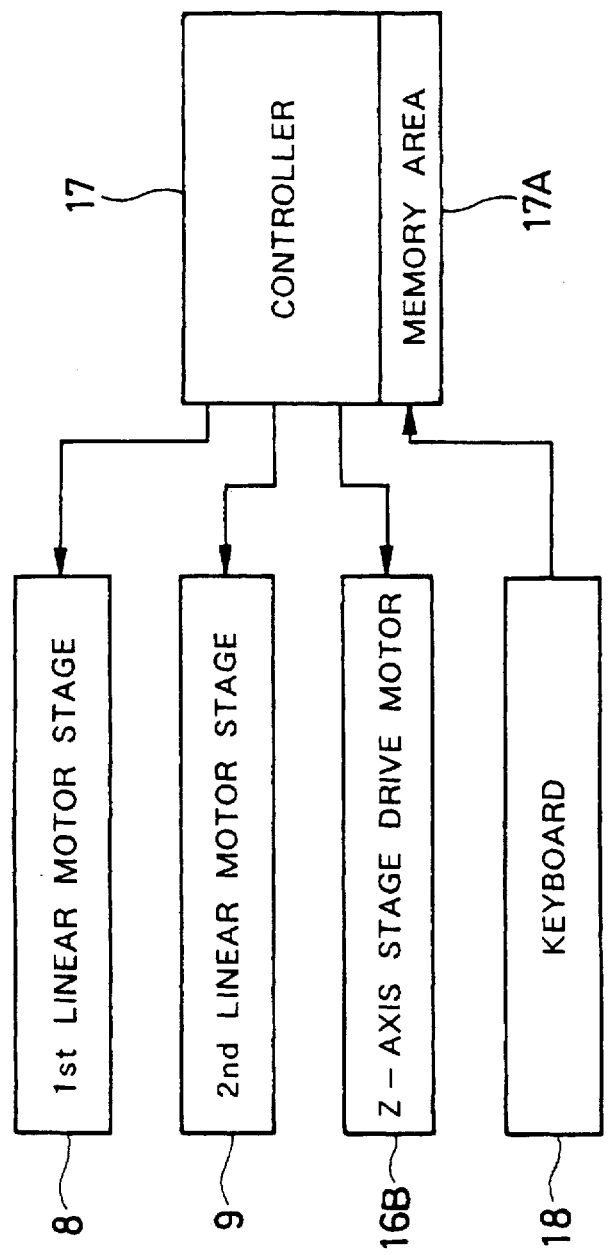
FIG. 6 is a block diagram of microtome circuit configuration.
Figure 7:
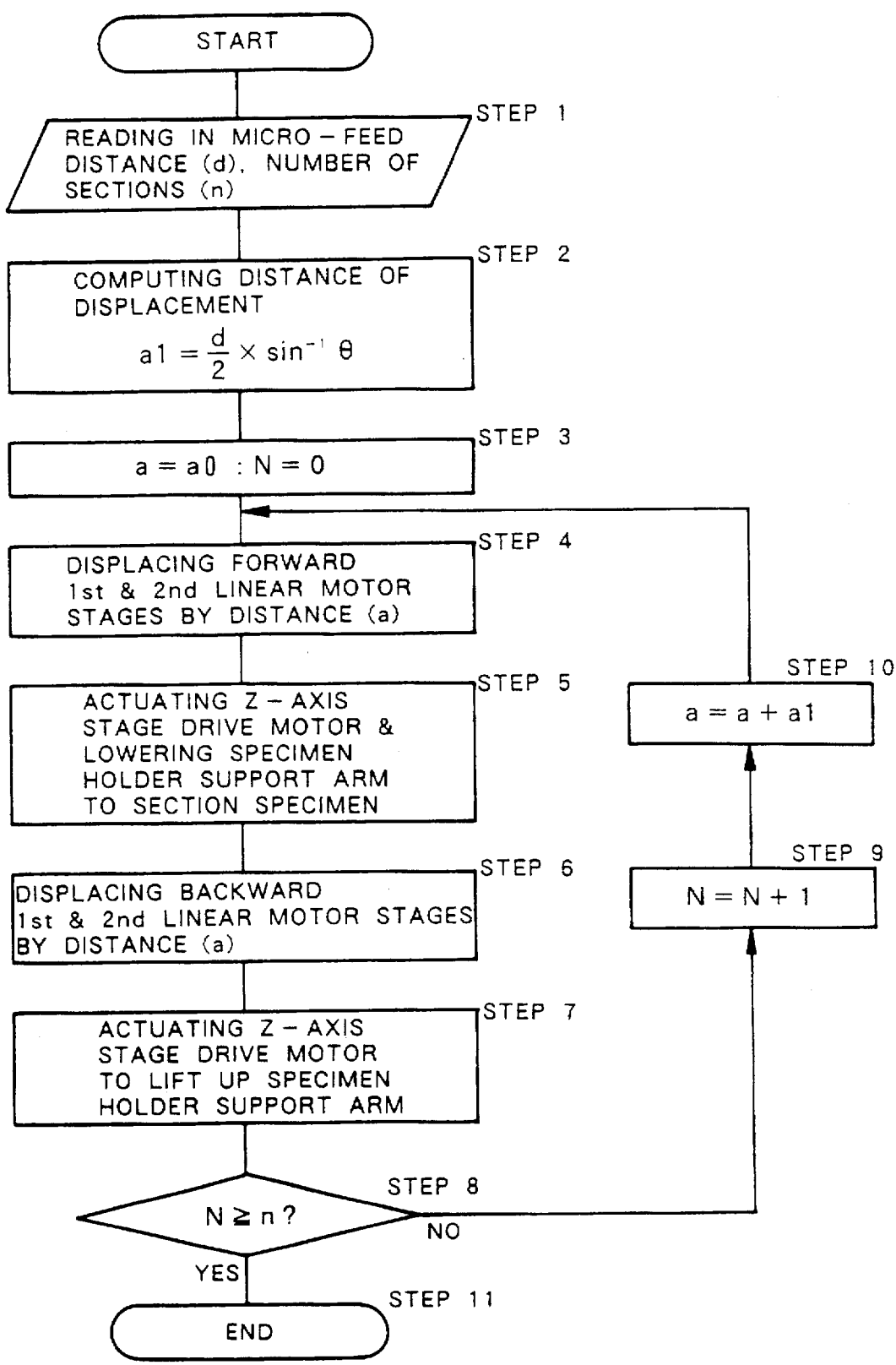
FIG. 7 is a flow chart of a microtome operation.

In FIG. 6, the reference numeral 17 indicates a controller which is in the form of a microcomputer or the like operating on a microtome action control program as shown in FIG. 7 according to preset values for the micro-feed distance "d" of the specimen 14 and number of sections "n" stored in its memory area 17A along with a distance of initial displacement "a0". Connected to the input interface of the controller 17 are keyboard 18 and other sensors and switches which are not shown in the drawing, and to the output interface are the first linear motor stage 8, second linear motor stage 9 and Z-axis stage drive motor 16B. The initial displacement "a0" determines an initial sectioning position on the specimen 14, regardless of the micro-feed distance "d".

Basic operations of the microtome 1 of the above-described construction are explained below in relation with the action control program shown in FIG. 7.

In the first place, before putting the microtome 1 in operation, the positions of the cutting knife 6 and specimen 14 are initialized according to predetermined initialization procedures. Namely, the cutting knife 6 is adjusted relative to the specimen 14 in the directions of X- and Y-axes by way of X-Y axis stage 3, while the escape angle of the cutting knife 6 is adjusted through adjustment of inclination angle of the tilting stage 4. On the other hand, inclination of the specimen 14 is adjusted by way of the tilting stage 4.

In the initialized positions, the specimen 14 and cutting knife 6 are spaced from each other in the direction of X-axis, and the specimen holder support arm 12 is located in an upper lifted position.

In the next place, the processing by the controller 17 is started from Step 1 to input the micro-feed distance "d" (or specimen piece thickness "d") and the number of sectioned specimen piece "n", then going to Step 2 to compute, on the basis of the input micro-feed distance "d", the distance of displacement "a1" of the first and second linear motor stages 8 and 9, $a1=d/2\times\sin^{-1}\theta$.

In Step 3, the distance "a0" of initial displacement is read out from the memory area 17A, and this initial displacement "a0" is set as the distance of displacement "a" and the counter N is set at "0".

Nextly, the movable blocks 8B and 9B of the first and second linear motor stages 8 and 9 are respectively displaced in forward directions, which are inverse to each other, by the distance "a" (equal to the distance of initial displacement a0) which was set in Step 3. As a consequence, the specimen 14, which is supported on the second movable block 9B through the Z-axis stage 11 and the specimen holder support arm 12, is displaced in the direction of X-axis by a distance: $2a0\times\sin\theta$.

Despite the displacement of the specimen holder support arm 12 in the direction of X-axis, the transmission rod 16C of the Z-axis stage drive 16 remains in the slot 12A of the specimen holder support arm 12 which is elongated in the direction of X-axis, transmitting a displacement in the direction of Z-axis from the Z-axis stage drive 16 to the specimen holder support arm 12.

In Step 5, the Z-axis stage drive motor 16B is actuated to slowly lower the specimen holder support arm 12. At this time, a tip end portion of the specimen 14 is hit against the cutting knife 6 which cuts off a first section of the specimen 14. The first section thus cut off the specimen 14 is floated on the water surface in the specimen collecting trough 6A. However, the first sectioning operation is performed only for the purpose of initializing the cutting and the resulting sectioned specimen piece is not used for microscopic inspection.

In Step 6, the movable blocks 8B and 9B of the first and second linear motor stages 8 and 9 are displaced backward respectively by the same distance "a", moving the specimen 14 away from the cutting knife 6 and preventing the specimen 14 from contacting the cutting knife 6 in the course the specimen holder support arm 12 is lifted upward.

In Step 7, the Z-axis stage drive motor 16B is actuated to lift up the specimen holder support arm 12 into the initial position.

Further, in Step 8, a check is made as to whether or not the number of sections reached "n" and, if judged "NO", which means that the preset number of specimen pieces have not yet been reached, the control goes to Step 9 to add "1" to the counter N and then to Step 10 to set a=a+a1 for the distance of displacement "a", followed by return to Step 4.

In the second round of processing from Step 4, the first and second linear motor stages 8 and 9 are displaced in Step 4 by the distance "a1" which corresponds to the micro-feed distance "d" from the initially cut tip end of the specimen 14. As a result, the tip end of the specimen 14 is protruded to such a degree as to pass over the cutting knife 6 by the distance $2a1\times\sin\theta$, namely, by the micro-feed distance "d". In Step 5, the specimen holder support arm 12 is slowly lowered by the Z-axis stage drive motor 16B, hitting the specimen 14 against the cutting knife 6 for a second sectioning operation. The resulting ultra-thin specimen piece is floated on the water surface within the specimen collecting trough 6A. Namely, this time the ultra-thin specimen piece is collected in the specimen collecting trough 6A for use.

Further, in Step 6, the movable blocks 8B and 9B of the first and second linear motor stages 8 and 9 are respectively displaced in backward directions, which are inverse to each other, and in Step 7 the specimen holder support arm 12 is lifted up into the initial position by the Z-axis stage drive motor 16B.

The processing from Step 4 to Step 7 is repeated to produce a number of ultra-thin specimen pieces of the thickness "d" and collect them in the specimen collecting trough 6A.

On the other hand, in case the judgement in Step 8 is "YES", which means that "n" number of ultra-thin specimen pieces have already been collected in the specimen collecting trough 6A, the control goes to Step 11 to end the microtome action control sequence.

Thus, the microtome of this embodiment, using the first and second linear motor stages 8 and 9 for the micro-feed mechanism 7, utilizes advantages of linear motors to guarantee accurate micro-feeds of the specimen 14, excluding conventional ball screws from the microtome mechanism to reduce inertial mass and to prevent back-lashes which would otherwise tend to occur to disturb accurate micro-feed operations.

The linear motor stages 8 and 9 of the micro-feed mechanism 7 are overlapped and intersected with each other in such a way as to form a small intersection angle $2\theta$ therebetween across the Y-axis, so that it becomes possible to minimize the micro-feed distance "d" by way of the intersection angle $2\theta$ even if the actual displacement distance "a" for the two linear motor stages is of a relatively large value.

In this regard, for example, in case the intersection angle $2\theta=15°$, the distance of displacement "a" and the micro-feed distance "d" are in the relations of d=0.26a. In case $2\theta=11.5°$, the displacement distance "a" and the micro-feed distance "d" are in the relations of d=0.2a. In case $2\theta=5°$, d=0.87a. If desired, the intersection angle can be set at a smaller angle such as 4° or 3°.

Accordingly, for example, in case the intersection angle $2\theta$ is set at 11.5 and the linear motor stage has a resolution power of 100 nm, it is possible to set the micro-feed distance "d" at about 20 nm at minimum to produce specimen pieces of 20 nm in thickness.

On the other hand, in case the intersection angle $2\theta$ is set at 11.5° and the linear motor stage has resolution power of 10 nm, theoretically the microtome 1 of this embodiment can cut ultra-thin specimen pieces as thin as 2 nm from the specimen. It follows that, by setting a suitable intersection angle $2\theta$, there can be easily produced ultra-thin specimen pieces which have thus far been difficult to prepare on conventional microtomes.

Further, in case the intersection angle $2\theta=5.0°$ and the resolution power of the linear motor stage is 100 nm, the micro-feed distance "d" can be set at about 10 nm at minimum to produce ultra-thin specimen pieces of 10 nm in thickness. In this instance, if the linear motor stage has a resolution power of 10 nm, theoretically the microtome 1 of this embodiment can produce ultra-thin specimen pieces of 1 nm in thickness.

Furthermore, the first and second linear motor stages 8 and 9 which are arranged in intersection relations with each other for displacements separately in the directions of X- and Y-axis make it possible to enhance the retentive force on the second movable block 9B which supports the Z-axis stage 11. This contributes to prevent escape of the specimen 14 when the cutting edge of the cutting knife 6 is hit thereagainst, suppressing deviations of the micro-feed distance "d" and thus permitting to set a micro-feed distance faithfully equivalent to the desired thickness of ultra-thin specimen piece.

On the other hand, the transmission rod 16C on the part of the Z-axis stage drive 16 is engaged in the slot 12A on the specimen holder support arm 12, thereby transmitting a displacement in the direction of the Z-axis from the Z-axis stage drive 16 to the specimen holder support arm 12 for moving up and down by means of the Z-axis drive 16. Therefore, when the specimen holder support arm 12 is driven up and down, vibrations of the Z-axis stage drive motor 16B of the Z-axis stage drive 16 are prevented from being directly transmitted to the specimen holder support arm 12, precluding possibilities of the specimen 14 at the fore end of the specimen holder support arm 12 being put in vibration as it is lowered at the time of a sectioning operation. Consequently, there can be obtained a specimen piece in the form of an ultra-thin section with neat clean cut surfaces free from undesirable undulations.

Thus, as described above, in the microtome of this embodiment, the first and second linear motor stages 8 and 9 of the micro-feed mechanism 7 are positioned in intersecting relations with each other. Accordingly, as compared with a set value for the distance of displacement "a", the micro-feed distance can be minimized to a significant degree by the effects of the intersection angle 2θ, making it possible to cut off ultra-thin specimen pieces correctly in a thickness equivalent with the micro-feed distance. As a result, the micro-feed mechanism 7 can easily produce ultra-thin specimen pieces of a thickness far smaller than resolution power of its own linear motor stages 8 and 9.

Figure 8:
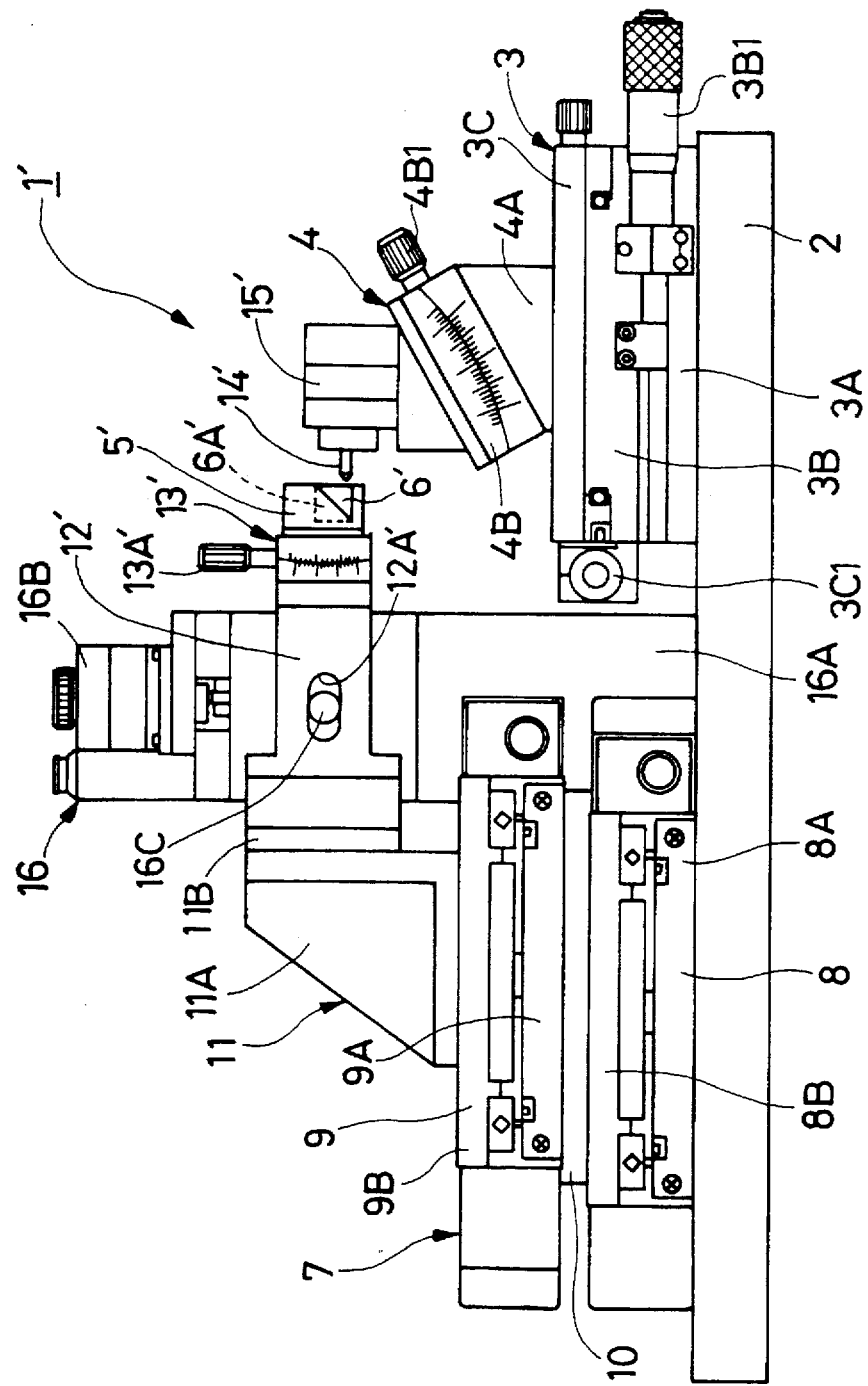
FIG. 8 is a schematic front view of another embodiment of the microtome according to the present invention.

Referring now to FIG. 8, there is shown a second embodiment of the present invention, in which a cutting knife is provided on the side of a micro-feed mechanism of a microtome 1' for movements toward and away from a specimen. In the following description of the second embodiment, those component parts common with the foregoing first embodiment are simply designated by similar reference numerals with an apostrophe "'" without repeating the same explanations.

In FIG. 8, indicated at 12' is a cutter holder support arm which has its base end securely fixed on a movable block 11B of a Z-axis stage 11 of the micro-feed mechanism 7. A cutting knife 6' is fixed on a cutter holder plate 5' which is securely fixed to the fore end of the cutter holder support arm 12' through a tilting stage 13'. Provided within the length of the cutter holder support 12' is a slot 12A' of a shape which is elongated in the direction of X-axis, for receiving therein the transmission rod 16C of the above-described Z-axis stage drive 16. Inclination of the cutter knife 6' is adjustable by means of the adjusting knob 13A of the tilting stage 13'.

Denoted at 15' is a specimen holder which holds thereon a frozen specimen material 14' and which is securely fixed on the tilting block 4B of the tilting stage 4 provided on the X-Y axes stage 3, in face to face relation with the micro-feed mechanism 7. Inclination of the specimen holder 15' is adjustable by means of the adjusting knob 4B1 of the tilting block 4B.

The microtome 1' of the arrangements just described operates substantially in the same manner as the microtome 1 of the foregoing first embodiment except that the cutting knife 6' is finely fed by the micro-feed mechanism 7. Therefore, for example, by feeding the cutting knife 6 from lower to upper side by the Z-axis stage drive 16, a specimen piece can be easily cut off from the specimen 14' and collected afloat on the distilled water surface within a specimen collecting trough 6A'.

In the foregoing embodiments of the present invention, the direction of displacement of the first linear motor stage 8 of the micro-feed mechanism 7 is tilted by +θ from the Y-axis while the direction of the second linear motor stage 9 is tilted by −θ from the Y-axis. However, it is to be understood that the present invention is not limited to these particular arrangements in angle and may employ different angles. For instance, if desired, the two linear motor stages 8 and 9 may be tilted from Y-axis by +α and −β, respectively. In such a case, the first and second linear motor stages 8 and 9 are displaced by different distances. Alternatively, the first and second linear motor stages 8 and 9 may be tilted at angles of +α and +β relative to the Y-axis, respectively, with an angle of intersection (α+β). In this case, the two linear motor stages 8 and 9 are displaced also by different distances to operate the micro-feed mechanism 7 as an X-axis motor stage.

Moreover, instead of linearly moving the specimen holder support arm 12 in the direction of Z-axis by the Z-axis stage 11 as described above, the specimen holder support arm 12 may be pivotally supported at its base end so that the specimen 14 at the fore end of the specimen holder support arm 12 is hit against the cutter knife 6 through an arcuate movement. In such a case, the specimen holder support arm 12 needs to be provided in a more lengthy form.

As clear from the foregoing detailed description, according to the present invention, the first and second feed means of the micro-feed mechanism are arranged to be displaced in two intersecting directions which are crossed by a predetermined intersection angle across Y-axis, for feeding either one of specimen or cutting knife toward the other over a small distance of an extremely fine level, permitting to make super-fine feeds as compared with resolution power of the first and second feed means and to cut specimen into ultra-thin specimen pieces exactly corresponding to super-fine feed distances.

Although the present invention has been described by way of its preferred embodiments, it will be possible for those skilled in the art to add various modifications or alterations thereto without departing from fundamental concept of the present invention.

What is claimed is:

1. A microtome, comprising:
    a machine base;
    a first holder means located on said machine base for holding one of a cutting knife and a specimen;
    a micro-feed mechanism located on said machine base side by side with said first holder means and having a feed direction toward said first holder means in an X-axis direction, including,
        a first feed means located on said machine base and having a feed in a direction offset by a first predetermined angle to a Y-axis direction, and
        a second feed means located on said first feed means and having a feed in a direction offset by a second predetermined angle to said Y-axis direction,
    wherein said feed of said first feed means combined with said feed of said second feed means produces a micro-feed of a distance (d) in said X-axis direction; and a second holder means located on said micro-feed mechanism adjacent to said first holder means to hold the other one of said cutting knife and said specimen not held by said first holder means.

2. A microtome as defined in claim 1, wherein said first feed means of said micro-feed mechanism is constituted by a first fixed member securely fixed on said machine base and a first movable member mounted movably on top of said first fixed member for movements in a direction at an angle of +θ with the Y-axis, direction, and said second feed means is constituted by a second fixed member securely fixed on said first movable member and a second movable member mounted movably on top of said second fixed member for movements in a direction at an angle of −θ with the Y-axis direction.

3. A microtome as defined in claim 2, wherein each of said first and second feed means of said micro-feed mechanisms is constituted by an individual linear motor stage, each linear motor stage including,

- a guide for linearly guiding movement of the respective movable member of said stage relative to the respective fixed member of said stage
- magnets fixedly mounted on said fixed member, and
- coils mounted on said movable member and supplied with current to produce magnetic fields for displacing the movable member by magnetic attracting and repelling actions against magnetic fields of the fixed magnets on said fixed member.

4. The microtome according to claim 1, wherein said distance (d) of said micro-feed in said X-direction is represented by the relationship, d=2a×sin θ, where

- said first predetermined angle is represented by θ,
- said second predetermined angle is −θ, and
- distance (a) represents an amount of feed of said first feed means also equivalent to an amount of feed of said second feed means.

5. The microtome according to claim 4, wherein said predetermined angle θ is set such that said distance (d) of said microfeed is smaller than 1/10 of (a).

6. A microtome, comprising:

- a machine base defining an XYZ coordinate system with X, Y, and X axes;
- a first linear stage located on the machine base for movements along directions of the X-axis and the Y-axis;
- a cutter holder provided on said first linear stage and holding a cutting knife thereon;
- a micro-feed mechanism including first and second linear motor stages provided on said machine base side by side with said first linear stage and feeding in the direction of the X-axis, said first linear motor stage being movably mounted on said machine base for displacements in a direction at a predetermined angle +θ with respect to the Y-axis, and said second linear motor stage being movably mounted on top of said first linear motor stage for displacements in a direction at a predetermined angle −θ with respect to the Y-axis;
- a second linear stage movably mounted on top of said second linear motor stage for displacements in a direction of the Z-axis;
- a specimen holder support arm provided on said second linear stage and supporting a specimen holder at a fore end thereof in confronting relation with said cutting knife; and
- a linear stage drive means for driving said specimen holder support arm in the direction of the Z-axis along with said second linear stage.

7. A microtome, comprising:

- a machine base defining an XYZ coordinate system with X, Y, and Z axes;
- a first linear stage located on the machine base for movements along directions of the X-axis and the Y-axis;
- a specimen holder provided on said first linear stage;
- a micro-feed mechanism including first and second linear motor stages provided on said machine base side by side with said first linear stage and feeding in the direction of the X-axis, said first linear motor stage being movably mounted on said machine base for displacements in a direction at a predetermined angle +θ with respect to the Y-axis, and said second linear motor stage being movably mounted on top of said first linear motor stage for movements in a direction at a predetermined angle −θ with respect to the Y-axis;
- a second linear stage movably mounted on top of said second linear motor stage of said micro-feed mechanism for displacements in a direction of the Z-axis;
- a cutter holder support arm provided on said second linear stage;
- a cutter holder supported on a fore end of said cutter holder support arm and holding a cutting knife for cutting a specimen in confronting relation with said specimen holder; and
- a linear stage drive means for driving said cutter holder support arm and said cutter holder in the direction of the Z-axis along with said second linear stage.

* * * * *